United States Patent
Lee et al.

(10) Patent No.: US 12,290,343 B2
(45) Date of Patent: May 6, 2025

(54) APPARATUS AND METHOD FOR ESTIMATING BIO-INFORMATION

(71) Applicant: SAMSUNG ELECTRONICS CO., LTD., Suwon-si (KR)

(72) Inventors: Tak Hyung Lee, Seoul (KR); Byung Hoon Ko, Hwaseong-si (KR); Seung Woo Noh, Seongnam-si (KR); Sang Yun Park, Hwaseong-si (KR); Jin Woo Choi, Ansan-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 355 days.

(21) Appl. No.: 17/748,187

(22) Filed: May 19, 2022

(65) Prior Publication Data
US 2023/0263412 A1 Aug. 24, 2023

(30) Foreign Application Priority Data
Feb. 21, 2022 (KR) .................. 10-2022-0022557

(51) Int. Cl.
*A61B 5/021* (2006.01)
*A61B 5/00* (2006.01)
*A61B 5/024* (2006.01)

(52) U.S. Cl.
CPC ...... *A61B 5/02116* (2013.01); *A61B 5/02125* (2013.01); *A61B 5/02416* (2013.01); *A61B 5/681* (2013.01); *A61B 5/7235* (2013.01)

(58) Field of Classification Search
None
See application file for complete search history.

(56) References Cited

U.S. PATENT DOCUMENTS

| | | | |
|---|---|---|---|
| 9,289,135 B2 | 3/2016 | LeBoeuf et al. | |
| 10,627,783 B2 | 4/2020 | Rothkopf et al. | |
| 10,813,561 B2 | 10/2020 | Kwon et al. | |
| 10,874,348 B1 | 12/2020 | Han et al. | |
| 2016/0206215 A1* | 7/2016 | Takahashi | A61B 5/681 |

(Continued)

FOREIGN PATENT DOCUMENTS

| | | | |
|---|---|---|---|
| JP | 2016119981 A | * | 7/2016 |
| JP | 2020-48943 A | | 4/2020 |

(Continued)

OTHER PUBLICATIONS

Fine et al., "Sources of Inaccuracy in Photoplethysmography for Continuous Cardiovascular Monitoring," Biosensors 2021, vol. 11, No. 126, 2021, Total 36 pages.

(Continued)

*Primary Examiner* — Mallika D Fairchild
(74) *Attorney, Agent, or Firm* — Sughrue Mion, PLLC

(57) ABSTRACT

An apparatus for estimating bio-information, may include: a main body; a photoplethysmogram (PPG) sensor disposed in the main body and configured to measure a PPG signal from an object of a user; an internal pressure sensor disposed in a closed space formed in the main body, and configured to measure a pressure applied to the closed space when the object applies force to a surface of the main body; and a processor configured to estimate the bio-information of the user based on the PPG signal and the pressure applied to the closed space.

10 Claims, 14 Drawing Sheets

(56) References Cited

U.S. PATENT DOCUMENTS

| | | |
|---|---|---|
| 2017/0086743 A1 | 3/2017 | Bushnell et al. |
| 2018/0184920 A1 | 7/2018 | Rabinovich et al. |
| 2019/0110758 A1* | 4/2019 | Kang .................... A61B 5/029 |
| 2020/0000351 A1 | 1/2020 | Rauhala |
| 2020/0037956 A1* | 2/2020 | Kang ................... A61B 5/0077 |
| 2020/0138373 A1 | 5/2020 | Shim et al. |
| 2020/0229743 A1* | 7/2020 | Choi ................. A61B 5/14551 |
| 2021/0030372 A1 | 2/2021 | Lizio et al. |

FOREIGN PATENT DOCUMENTS

| | | |
|---|---|---|
| KR | 10-2011-0111827 A | 10/2011 |
| KR | 10-2016-0086563 A | 7/2016 |
| KR | 10-2018-0076050 A | 7/2018 |
| KR | 10-2019-0070573 A | 6/2019 |
| KR | 10-2020-0052164 A | 5/2020 |
| WO | 2018/127774 A1 | 7/2018 |

OTHER PUBLICATIONS

Teng et al., "The effect of contacting force on photoplethysmographic signals," IPO science, Physiological Measurement, vol. 25, No. 5, 2004, Total 3 pages (Abstract only).
Communication dated Jul. 26, 2024, issued by the Korean Patent Office in Korean Application No. 10-2022-0022557.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2022-0022557, filed on Feb. 21, 2022, in the Korean Intellectual Property Office, the disclosure of which is incorporated herein by reference in its entirety.

BACKGROUND

1. Field

Apparatuses and methods consistent with example embodiments relate to non-invasively estimating bio-information.

2. Description of the Related Art

Research on information technology (IT)-medical convergence technology, in which IT and medical technology are combined, is being recently carried out to address the aging population structure, rapid increase in medical expenses, and shortage of specialized medical service personnel. Particularly, monitoring of the health condition of the human body is not limited to a fixed place, such as a hospital, but is expanding to a mobile healthcare sector for monitoring a user's health status at any time and any place in daily life at home and office. Electrocardiography (ECG), photoplethysmogram (PPG), and electromyography (EMG) signals are examples of bio-signals that indicate the individual's health condition. Various bio-signal sensors are being developed to measure these signals in daily life.

SUMMARY

According to an aspect of the present disclosure, an apparatus for estimating bio-information, may include: a main body; a photoplethysmogram (PPG) sensor disposed in the main body and configured to measure a PPG signal from an object of a user; an internal pressure sensor disposed in a closed space formed in the main body, and configured to measure a pressure applied to the closed space when the object applies force to a surface of the main body; and a processor configured to estimate the bio-information of the user based on the PPG signal and the pressure applied to the closed space.

Based on a change in volume of the closed space due to the force applied to the surface of the main body, the internal pressure sensor may be configured to measure the pressure applied to the closed space.

The main body may include a housing having the closed space formed therein.

The closed space may be completely sealed.

The closed space may be formed in only a portion of an internal space of the housing on a side that comes into contact with the object.

The housing may include an upper region in which a display is mounted, and a lower region that comes into contact with the object, wherein the closed space may be formed in the lower region of the housing.

The main body may include a container having the closed space formed therein.

The container and the PPG sensor may be disposed side-by-side on a same surface.

The processor may be further configured to determine a contact pressure between the object and the PPG sensor based on the pressure applied to the closed space.

The apparatus may include an external atmospheric pressure sensor configured to measure an external atmospheric pressure.

The processor may be further configured to determine the contact pressure between the object and the PPG sensor based further on the external atmospheric pressure.

The processor may be further configured to estimate blood pressure of the user by analyzing the PPG signal according to the contact pressure between the object and the PPG sensor.

The apparatus may further include a display configured to output at least one of the contact pressure between the object and the PPG sensor, guide information for guiding the user to change the contact pressure, and a bio-information estimation result.

According to another aspect of the present disclosure, a method of estimating bio-information by an electronic device, may include: by using a photoplethysmogram (PPG) sensor, measuring a PPG signal from an object of a user; by using an internal pressure sensor disposed in a closed space formed in the electronic device, measuring a pressure applied to an inside of the closed space when the object contacts and applies force to a measurement surface of the PPG sensor of the electronic device; and estimating bio-information of the user based on the PPG signal and the pressure applied to the closed space.

The measuring of the pressure applied to the closed space may include measuring the pressure applied to the inside of the closed space based on a change in volume of the closed space due to the force applied by the object to the measurement surface of the electronic device.

The estimating of the bio-information of the user may further include determining a contact pressure between the object and the PPG sensor based on the pressure applied to the inside of the closed space.

The determining of the contact pressure between the object and the PPG sensor may include measuring an external atmospheric pressure.

The determining of the contact pressure between the object and the PPG sensor may include determining the contact pressure between the object and the PPG sensor based further on the external atmospheric pressure.

The estimating of the bio-information of the user may include estimating blood pressure of the user by analyzing the PPG signal according to the contact pressure between the object and the PPG sensor.

According to another aspect of the present disclosure, there is provided a non-transitory computer-readable storage medium storing a program that is executable by a computer to perform a method of estimating bio-information. The method may include: obtaining a photoplethysmogram (PPG) signal that is measured from an object by an PPG sensor; obtaining an internal pressure of the PPG sensor while the object is in contact with a measurement surface of the PPG sensor; obtaining an external pressure of the PPG sensor that is measured at a time when the PPG signal and the internal pressure are obtained; and estimating blood pressure of the object based on the PPG signal, the internal pressure of the PPG sensor, and the external pressure of the PPG sensor.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
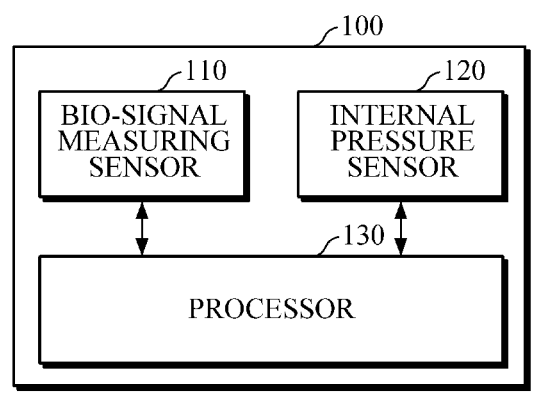
FIG. 1 is a block diagram illustrating an apparatus for estimating bio-information according to an example embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for estimating bio-information will be described in detail with reference to the accompanying drawings.

FIG. 1 is a block diagram illustrating an apparatus for estimating bio-information according to an example embodiment of the present disclosure. An apparatus 100 for estimating bio-information may include at least one or more of a wearable device, such as a wristwatch-type wearable device, a bracelet-type wearable device, a wristband-type wearable device, a ring-type wearable device, a glasses-type wearable device, a headband-type wearable device, etc., a smartphone, a cellular phone, a wristwatch, various medical devices (short wave infrared camera, long wave infrared camera, etc.), and a combination thereof.

Referring to FIG. 1, an apparatus 100 for estimating bio-information may include a bio-signal measuring sensor 110, an internal pressure sensor 120, and a processor 130.

The apparatus 100 for estimating bio-information may estimate a user's bio-information based on a measured bio-signal. In this case, the bio-information may include blood pressure, antioxidant index, blood glucose, lactate, alcohol, cholesterol, triglyceride, etc., but is not limited thereto.

The bio-signal measuring sensor 110 may be disposed in a main body of the apparatus 100 for estimating bio-information.

The bio-signal measuring sensor 110 may include a photoplethysmography (PPG) sensor, an electrocardiography (ECG) sensor, an electromyography (EMG) sensor, etc., and may measure a PPG signal, an ECG signal, and the like from a user's object. However, the type of the bio-signal measuring sensor 110 and the type of the measured bio-signal are not limited thereto and may be changed variously.

The object may be a surface of the wrist that is adjacent to the radial artery and an upper part of the wrist where venous blood or capillary blood passes, or may be a peripheral part of a human body, such as fingers, toes, ears, etc., where blood vessels are densely distributed in the human body, but is not limited thereto.

The bio-signal measuring sensor 110 may include a light source for emitting light onto the object, and a detector for detecting emanating light scattered or reflected from body tissue of the object after light is emitted by the light source onto the object.

In this case, the light source may include at least one of a light emitting diode (LED), a laser diode (LD), a phosphor, etc., but is not limited thereto. The detector may include a photodiode, a photo transistor, a photodiode array, a photo transistor array, an image sensor (e.g., complementary metal-oxide semiconductor (CMOS) image sensor), and the like. A plurality of light sources may emit light of the same wavelength or light of different wavelengths. For example, the light sources may emit light of green, blue, red, and infrared wavelengths, etc., but are not limited thereto. A plurality of detectors may be positioned at different distances from the light source.

The bio-signal measuring sensor 110 may further include an additional component required for measuring the bio-signal. For example, the bio-signal measuring sensor 110 may further include an amplifier for amplifying an electrical signal output by the detector that detects light, an analog-to-digital converter for converting an electrical signal, output by the detector or the amplifier, into a digital signal, and the like. In addition, in the case where the bio-signal measuring sensor 110 measures the ECG signal, a plurality of electrodes may be included in the bio-signal measuring sensor 110.

The internal pressure sensor 120 may be disposed in a closed space formed in the main body of the apparatus 100 for estimating bio-information. The internal pressure sensor 120 may measure pressure applied to the inside of the closed space when the object is placed on one surface of the main body of the apparatus 100 for estimating bio-information and applies force thereto.

For example, the internal pressure sensor 120 may measure the pressure applied to the inside of the closed space by using the following Equation 1, but is not limited thereto.

$$P \cdot V = C \quad \text{[Equation 1]}$$

In this case, P denotes the pressure applied by the object to the inside of the close space; V denotes a volume of the close space; and C denotes a fixed constant. That is, when the object is placed on one surface of the main body of the apparatus 100 for estimating bio-information and applies force thereto, the internal pressure sensor 120 may measure a change in volume of the closed space due to mechanical deformation of a structure (e.g., housing, block, etc.) having the closed space formed therein, and may measure the pressure applied to the inside of the closed space based on the measured change in volume of the closed space.

The closed space, in which the internal pressure sensor 120 is disposed, may be formed in at least one of the entire main body housing of the apparatus 100 for estimating bio-information, a portion of the internal space of the main body housing, and a block (e.g., a container) disposed at a position where a relatively large mechanical deformation occurs. An example of a structure of the apparatus 100 for estimating bio-information will be described below with reference to FIGS. 2 to 3C.

Figure 2:
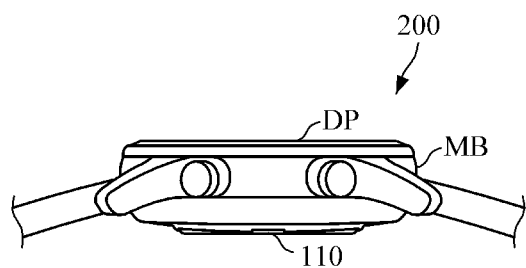
FIG. 2 is a diagram illustrating an example of an apparatus for estimating bio-information.

FIG. 2 is a diagram illustrating an example of an apparatus for estimating bio-information. FIG. 2 is a diagram illustrating an apparatus 200 for estimating bio-information which is implemented as a wristwatch-type wearable device. However, as illustrated above in FIG. 1, a shape of the apparatus for estimating bio-information is not limited thereto and may be changed to various shapes.

FIG. 2 illustrates an example in which the apparatus 200 for estimating bio-information includes a main body MB, a display DP as an example of an output interface mounted on a front surface of the main body MB, and the bio-signal measuring sensor 110 mounted on a rear surface of the main body.

Various structures having a closed space formed in the main body MB will be described below with reference to FIGS. 3A to 3C. In some example embodiments of the present disclosure, the closed space may be completely sealed to prevent air, liquid, or particles from moving in or out.

Figure 3A:
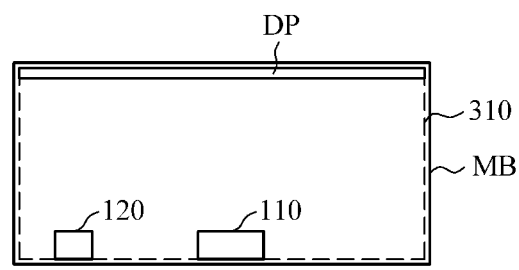
FIGS. 3A to 3C are diagrams illustrating examples of a closed space formed in a main body.
Figure 3B:
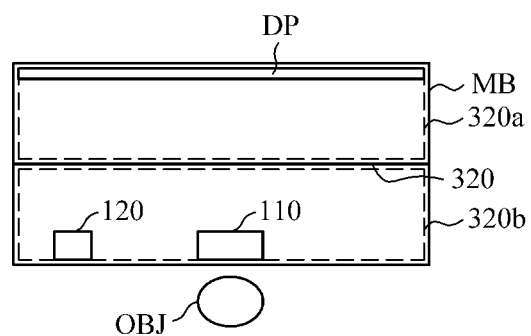
Figure 3C:
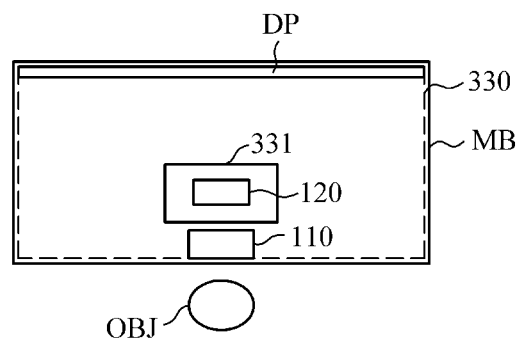

FIGS. 3A to 3C are diagrams illustrating examples of a closed space formed in a main body. FIG. 3A illustrates an example of the closed space formed throughout the entire internal space of the main body housing; FIG. 3B illustrates an example of the closed space formed in a portion of the main body housing; and FIG. 3C illustrates an example of the closed space formed in a block.

Referring to FIG. 3A, an example is illustrated in which the apparatus for estimating bio-information includes the main body MB, the display DP mounted on a front surface of the main body, a main body housing 310, the bio-signal measuring sensor 110, and the internal pressure sensor 120.

FIG. 3A illustrates a structure in which the main body housing 310 includes the display DP. That is, FIG. 3A illustrates an example in which the display DP is disposed in the main body housing 310, such that an upper surface of the main body housing 310 comes into contact with an upper surface of the display DP. However, the display DP is not limited thereto and may be disposed in an independent space separately from the main body housing 310.

The closed space may be formed throughout the entire internal space of the main body housing 310. In this case, the housing 310 may be made of a material for preventing passage of air between the inside and the outside of the main body MB. In this case, the housing 310 may be made of, for example, a material having a waterproof function, but is not limited thereto.

The internal pressure sensor 120 may be disposed on one side of the main body housing 310 formed as the closed space, such that when the object is placed on one surface of the main body MB and applies force thereto, the internal pressure sensor 120 may measure pressure applied to the inside of the main body housing 310. For example, the internal pressure sensor 120 may measure the pressure applied to the inside of the closed space based on a change in volume of the internal space of the main body housing 310 due to the force applied by the object to the one surface of the main body MB.

While FIG. 3A illustrates an example in which the internal pressure sensor 120 is disposed on the left side of the bio-signal measuring sensor 110, the internal pressure sensor 120 is not limited thereto, and the arrangement and position of the bio-signal measuring sensor 110 and the internal pressure sensor 120 may be changed variously.

Referring to FIG. 3B, an example is illustrated in which the apparatus for estimating bio-information includes the main body MB, an upper region 320a of the main body housing, a lower region 320b of the main body housing, an interface 320 between the upper and lower regions, the display DP as an example of an output interface, the bio-signal measuring sensor 110, and the internal pressure sensor 120.

While FIG. 3B illustrates a structure in which the upper region 320 of the main body housing includes the display DP, the display DP is not limited thereto and may be disposed in an independent space separately from the upper region 320 of the main body housing, similarly to the above example of FIG. 3A. A detailed description thereof will be omitted.

The upper region 320a of the main body housing may be a region where an output interface, e.g., the display DP, is mounted for visually providing a user with contact pressure between an object OBJ and the bio-signal measuring sensor 110, guide information for guiding a change in the contact pressure, a bio-information estimation result, and the like.

The lower region 320b of the main body housing may be a region in the main body housing that comes into contact with the object OBJ, e.g., a body part such as the upper part of the wrist, a finger, etc., as illustrated in FIG. 1.

The upper region 320a of the main body housing and the lower region 320b of the main body housing may be separated by the interface 320 between the upper and lower regions.

The closed space may be formed in only a portion of the internal space of the main body housing.

For example, the closed space may be formed in any one of the upper region 320a and the lower region 320b of the main body housing. In this case, the interface 320 between the upper and lower regions may be made of a material for preventing passage of air between the upper region 320a and the lower region 320b of the main body housing, thereby preventing air from entering into the upper region 320a and the lower region 320b of the main body housing. In this case, the interface 320 between the upper and lower regions may be made of, for example, a material having a waterproof function, but is not limited thereto.

FIG. 3B illustrates an example in which the internal pressure sensor 120 is disposed in the lower region 320b of the main body housing, and the closed space is formed in the lower region 320b of the main body housing. However, the closed space is not limited thereto and may be formed in the upper region 320a of the main body housing; or if the main body housing is divided into the left and right sides rather than into the upper and lower sides, the closed space may be formed in the left region or the right region of the main body housing.

Referring to FIG. 3B, the internal pressure sensor 120 may be disposed on one side of lower region 320b of the main body housing which is formed as the closed space, such that when the object OBJ is placed on one surface of the main body MB and applies force thereto, the internal pressure sensor 120 may measure pressure applied to the inside of the lower region 320b of the main body housing 310. For example, the internal pressure sensor 120 may measure the pressure applied to the inside of the closed space based on a change in volume of the internal space of the lower region 320b of the main body housing due to the force applied by the object to the one surface of the main body MB.

Upon comparison of FIGS. 3A and 3B, FIG. 3A illustrates an example in which the entire space of the main body housing 310 is formed as the closed space, and FIG. 3B illustrates an example in which only the lower region 320b of the main body housing is formed as the closed space. In this case, if the closed space has a relatively small size as illustrated in FIG. 3B, a change in volume of the closed space due to the force applied by the object may be reflected accurately, such that contact pressure between the apparatus for estimating bio-information and the object may be determined with improved accuracy.

Referring to FIG. 3C, an example is illustrated in which the apparatus for estimating bio-information includes the main body MB, a main body housing 330, a block (e.g., a container) 331, the bio-signal measuring sensor 110, and the internal pressure sensor 120.

While FIG. 3C illustrates a structure in which the main body housing 330 includes the display DP, the display DP is not limited thereto and may be disposed in an independent space separately from the main body housing 330, similarly to the above example of FIG. 3A. A detailed description thereof will be omitted.

The block 331 may be disposed in the main body MB and/or the internal space of the main body housing 330. For example, the block 331 may be disposed at a position where a relatively large mechanical deformation occurs in the main body MB and/or the main body housing 330.

For example, as illustrated in FIG. 3C, in the case where the object OBJ comes into contact with the lower region of the main body MB, a large mechanical deformation occurs due to the force applied by the object OBJ in the lower region rather than the upper region of the main body MB, such that the block 331 may be disposed to be biased to the lower region of the main body MB. In this case, the object OBJ is generally placed at a position where the bio-signal measuring sensor 110 is disposed, such that the block 331 may be disposed adjacent to the bio-signal measuring sensor 110, but is not limited thereto.

The block 331 may have an internal space which is formed as a closed space and may include the internal pressure sensor 120. In this case, the block 331 may be formed as a material having a waterproof function and the like, so as to block the internal space of the block 331 from the outside. However, the material of the block 331 and the like may be changed variously.

The internal pressure sensor 120 may be disposed on one side of the block 331 formed as the closed space, such that when the object OBJ is placed on one surface of the main body MB and applies force thereto, the internal pressure sensor 120 may measure pressure applied to the inside of the block 331. For example, the internal pressure sensor 120 may measure the pressure applied to the inside of the closed space based on a change in volume of the internal space of the block 331 due to the force applied by the object to the one surface of the main body MB.

Upon comparison of FIGS. 3A to 3C, FIG. 3A illustrates an example in which the entire space of the main body housing 310 is formed as the closed space, FIG. 3B illustrates an example in which only the lower region 320b of the main body housing is formed as the closed space, and FIG. 3C illustrates an example in which the closed space is separately formed in only the block 331 inside the main body. In this case, if the size of the closed space decreases in the order of from FIG. 3A to 3C, a change in volume of the closed space due to the force applied by the object may be reflected accurately, such that contact pressure between the apparatus for estimating bio-information and the object may be determined with improved accuracy. In addition, the block 331 of FIG. 3C is disposed at a position where a relatively large mechanical deformation occurs in the main body housing 330, e.g., is disposed adjacent to the bio-signal measuring sensor, such that a change in volume of the closed space due to the force applied by the object may be reflected more accurately.

Referring back to FIG. 1, the processor 130 may estimate a user's bio-information based on the measured bio-signal and the pressure applied to the closed space.

For example, the processor 130 may determine contact pressure between the object and the bio-signal measuring sensor 110, and may estimate a user's bio-information based on the determined contact pressure between the object and the bio-signal measuring sensor 110.

For example, the processor 130 may determine the contact pressure between the object and the bio-signal measuring sensor 110 by applying the measured pressure, applied to the closed space, to a predetermined contact pressure estimation model as represented by the following Equation 2, but is not limited thereto.

$$y = ax + b \quad \text{[Equation 2]}$$

Herein, y denotes the contact pressure to be obtained; x denotes the measured pressure applied to the closed space; and a and b denote values pre-calculated by preprocessing, and may be defined differently according to the size of the closed space, a material of a structure (e.g., housing, block, etc.) formed as the closed space, an arrangement of the closed space, and the like.

In this case, if the determined contact pressure falls outside a predetermined range, the processor 130 may guide the object to gradually increase force when the object is in contact with the bio-signal measuring sensor 110, or may guide the object to gradually decrease a pressing force after the object applies a force which is greater than or equal to a predetermined threshold value, or by contrast may guide the object to gradually decrease pressure after the object applies contact pressure which is greater than or equal to a predetermined initial threshold value. For example, the processor 130 may provide a user with guide information for guiding the user to change contact pressure by using a display module, an audio output module, and the like mounted in the apparatus 100 for estimating bio-information or in an external device connected thereto.

The processor 130 may estimate the user's bio-information by analyzing a bio-signal according to the determined contact pressure between the object and the bio-signal measuring sensor 110. For convenience of explanation, the following description will be given using a PPG signal as the bio-signal and blood pressure as the bio-information.

The processor 130 may estimate the user's blood pressure based on an oscillometric waveform envelope generated based on the measured PPG signal and the determined contact pressure.

In this case, the processor 130 may generate the oscillometric waveform envelope based on the measured PPG signal and the determined contact pressure, which will be described below with reference to FIG. 3D.

Figure 3D:
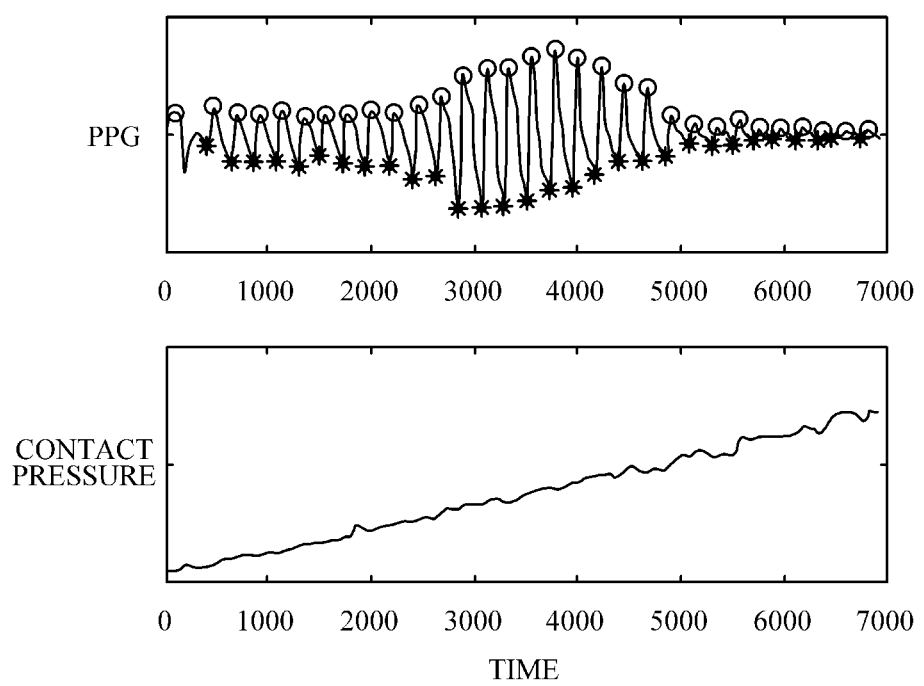
FIG. 3D is a diagram illustrating a PPG signal measured from an object and contact pressure.

FIG. 3D is a diagram illustrating a PPG signal measured from an object by the bio-signal measuring sensor 110 and contact pressure. As illustrated herein, when a user places an object on the bio-signal measuring sensor 110 and gradually increases pressure, the amplitude of a pulse wave also gradually increases during a predetermined period of time.

The processor 130 may extract a peak-to-peak point by subtracting a negative (−) amplitude value from a positive (+) amplitude value of a waveform envelope of the pulse wave signal at each measurement time point, and by plotting the extracted peak-to-peak amplitude at each measurement time point against a contact pressure value at a corresponding time point, the processor 130 may obtain an oscillometic waveform envelope that represents the pressure versus pulse wave.

In this case, the processor 130 may preprocess the generated oscillometric waveform envelope. For example, the processor 130 may smooth the generated oscillometric waveform envelope. In this case, the processor 130 may smooth the generated oscillometric waveform envelope by using a moving sum, a moving average, polynomial fitting, Gaussian fitting, and the like. In another example, the processor 130 may obtain a derivative signal by differentiating the obtained oscillometric waveform envelope or the smoothed oscillometric waveform envelope. In yet another example, the processor 130 may normalize the generated oscillometric waveform envelope. However, the preprocessing is not limited thereto.

The processor 130 my extract one or more features from the generated oscillometric waveform envelope and/or the preprocessed oscillometric waveform envelope, and may estimate a user's blood pressure based on the extracted features, which will be described in detail below with reference to FIG. 3E.

Figure 3E:
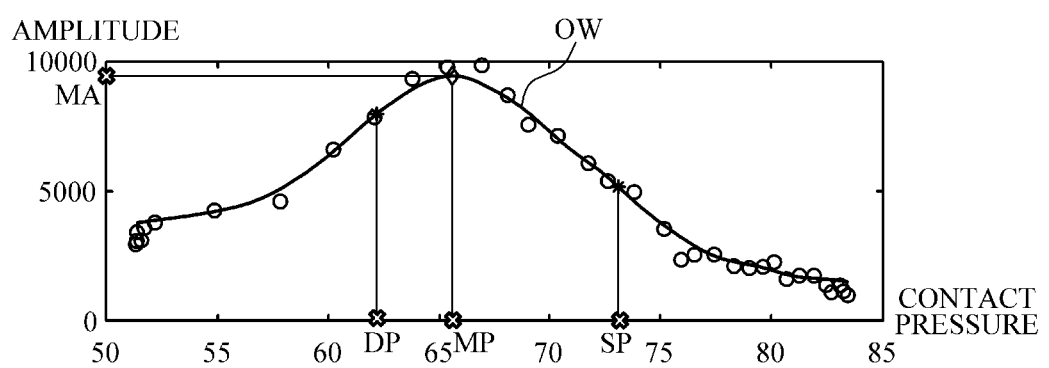
FIG. 3E is a diagram illustrating an example of an oscillometric waveform envelope.

FIG. 3E is a diagram illustrating an example of an oscillometric waveform envelope.

Referring to FIG. 3E, the processor 130 may extract, as features, an amplitude value MA at a maximum peak point or a contact pressure value MP at the maximum peak point, and contact pressure values SP and DP at points to the left and right of the maximum peak point MA and having a predetermined ratio (e.g., 0.5 to 0.7) to the contact pressure value MP at the maximum peak point MA.

Upon extracting one or more features from the oscillometic waveform envelope, the processor 130 may estimate a user's blood pressure based on the extracted features.

For example, the processor 130 may estimate, as Mean Arterial Pressure (MAP), the contact pressure value MP at the maximum peak point, which is extracted from the oscillometic waveform envelope. In addition, the processor 130 may calculate, as systolic blood pressure (SBP), a contact pressure value SP at a point to the right of the maximum peak point and having a predetermined ratio to the contact pressure value MP at the maximum peak point, and may calculate, as diastolic blood pressure (DBP), a contact pressure value DP at a point to the left of the maximum peak point and having a predetermined ratio to the contact pressure value MP at the maximum peak point.

In another example, the processor 130 may estimate a user's blood pressure by using a predetermined bio-information estimation model that define a relationship between the extracted feature and the user's blood pressure.

Figure 4A:
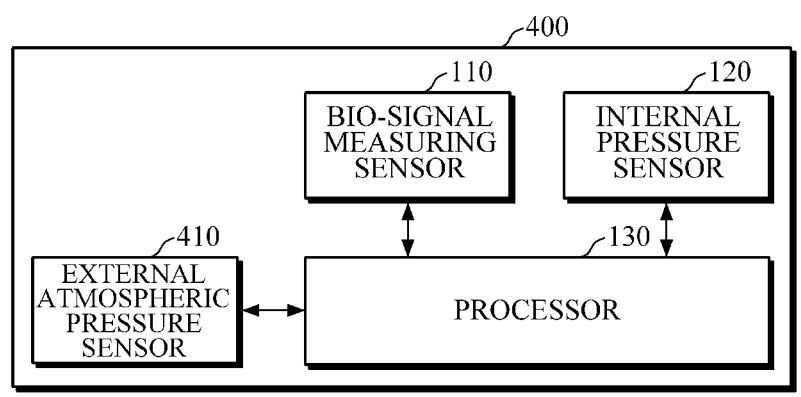
FIG. 4A is a block diagram illustrating an apparatus for estimating bio-information according to another example embodiment of the present disclosure.

FIG. 4A is a block diagram illustrating an apparatus for estimating bio-information according to another example embodiment of the present disclosure. Referring to FIG. 4A, an apparatus 400 for estimating bio-information may further include an external atmospheric pressure sensor 410, in addition to the bio-signal measuring sensor 110, the internal pressure sensor 120, and the processor 130 which are described above. The following description will be focused on the external atmospheric pressure sensor 410, and a redundant description will be omitted.

The external atmospheric pressure sensor 410 is disposed on one surface inside the main body and may measure external atmospheric pressure of the apparatus 400 for estimating bio-information. For example, the external atmospheric pressure 410 may measure atmospheric pressure of outside air that passes through holes formed in the main body housing.

Figure 4B:
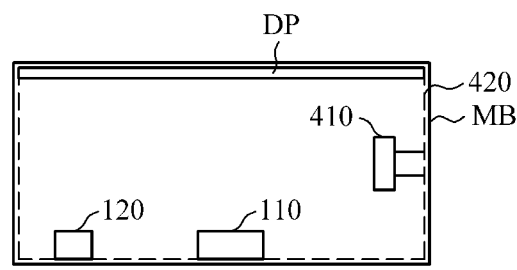
FIG. 4B is a diagram illustrating an example of a main body of the apparatus for estimating bio-information of FIG. 4A.

FIG. 4B is a diagram illustrating an example of the main body of the apparatus for estimating bio-information of FIG. 4A.

While FIG. 4B illustrates a structure in which a main body housing 420 includes a display DP, the display DP is not limited thereto and may be disposed in an independent space separately from the main body housing 420, similarly to the above example of FIG. 3A. A detailed description thereof will be omitted.

Referring to FIG. 4B, the external atmospheric pressure sensor 410 may be disposed on one side of the main body MB. While FIG. 4B illustrates an example in which the external atmospheric pressure sensor 410 is disposed at the center of a right surface of the main body housing 420, the position of the external atmospheric pressure sensor 410 is not limited thereto.

A surface of the main body housing 420, which corresponds to the external atmospheric pressure sensor 410, i.e., a contact surface between the main body housing 420 and the external atmospheric pressure sensor 410, may have holes through which outside air may pass. In this case, the external atmospheric pressure sensor 410 may measure atmospheric pressure of the outside air passing through the holes formed in the main body housing 420.

Referring back to FIG. 4A, the processor 130 may determine the contact pressure between the object and the bio-signal measuring sensor 110 by applying the atmospheric pressure, measured by the external atmospheric pressure sensor 410, along with the measured pressure applied to the closed space, to a predetermined contact pressure estimation model, but the contact pressure is not limited thereto.

$$y=cx+dz+e \qquad \text{[Equation 3]}$$

Herein, y denotes the contact pressure to be obtained; x denotes the measured pressure applied to the closed space; z denotes the measured external atmospheric pressure; and c, d, and e denote values pre-calculated by preprocessing, and may be defined differently according to the size of the closed space, a material of a structure (e.g., housing, block, etc.) formed as the closed space, the arrangement of the closed space, the type of the external atmospheric pressure sensor, the arrangement of the external atmospheric pressure sensor, and the like.

That is, when the internal pressure sensor 120 measures the pressure applied to the inside of the closed space, the measured pressure is under the influence of external atmospheric pressure, as well as the influence of pressure applied by the object. In this case, by subtracting the influence of external atmospheric pressure (e.g., dz in the above Equation) based on the external atmospheric pressure measured by the external atmospheric pressure sensor 410, the processor 130 may determine the contact pressure between the object and the bio-signal measuring sensor 110 with improved accuracy.

Figure 5A:
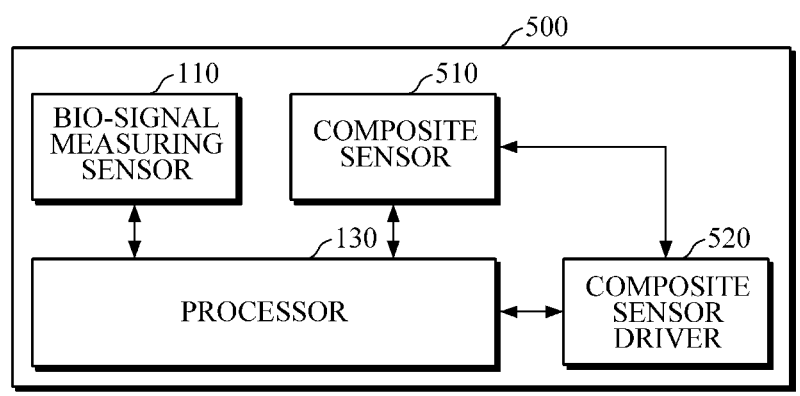
FIG. 5A is a block diagram illustrating an apparatus for estimating bio-information according to yet another example embodiment of the present disclosure.

FIG. 5A is a block diagram illustrating an apparatus for estimating bio-information according to yet another example embodiment of the present disclosure.

Referring to FIG. 5A, an apparatus 500 for estimating bio-information may include the bio-signal measuring sensor 110, the processor 130, a composite sensor 510, and a composite sensor driver 520. The bio-signal measuring sensor 110 and the processor 130 are described above with reference to FIG. 1, such that the composite sensor 510 and the composite sensor driver 520 will be described in detail below.

The composite sensor 510 may be disposed in a closed space formed in a main body of the apparatus 500 for estimating bio-information. In this case, the closed space may be disposed in any one of the closed spaces described above with reference to FIGS. 3A to 3C, but is not limited thereto.

The composite sensor driver 520 may be electrically connected to the processor 130, and may drive the composite sensor 510 under the control of the processor 130. For example, the composite sensor driver 520 may drive the composite sensor 510 in a time-division manner, to measure pressure applied by the object to the inside of the closed space, or to measure external atmospheric pressure of the apparatus 500 for estimating bio-information, which will be described in detail below with reference to FIGS. 5B and 5C.

Figure 5B:
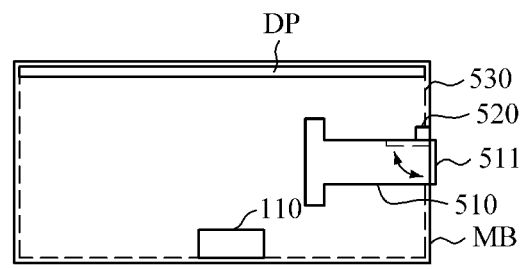
FIGS. 5B and 5C are diagrams illustrating an example of a main body of the apparatus for estimating bio-information of FIG. 5A.
Figure 5C:
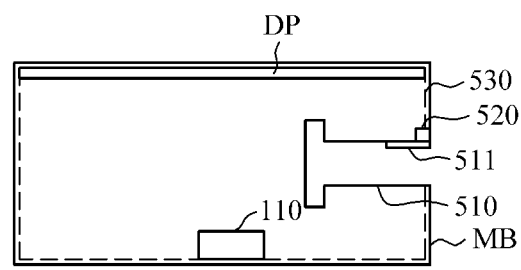

FIGS. 5B and 5C are diagrams illustrating an example of the main body of the apparatus 500 for estimating bio-information of FIG. 5A. Referring to FIGS. 5B and 5C, the main body MB of the apparatus 500 for estimating bio-information may include a main body housing 530, the bio-signal measuring sensor 110, the composite sensor 510, and the composite sensor driver 520.

While FIGS. 5B and 5C illustrate a structure in which the main body housing 530 includes the display DP, the display DP is not limited thereto and may be disposed in an independent space separately from the main body housing 530, similarly to the above example of FIG. 3A. A detailed description thereof will be omitted.

While FIGS. 5B and 5C illustrate an example in which the composite sensor 510 is disposed at the center of a right surface of the main body housing 530, the position of the composite sensor 510 is not limited thereto and may be changed variously. While FIGS. 5B and 5C illustrate an example in which a closed space is formed throughout the entire main body housing 530, the closed space may be formed in a portion of the main body housing or may be formed separately in a block, as illustrated in FIGS. 3B and 3C. A detailed description thereof will be omitted.

The composite sensor 510 may include an opening and closing part 511 which is opened and closed by the operation of the composite sensor driver 520.

FIG. 5B illustrates an example in which the opening and closing part 511 is closed, and FIG. 5C illustrates an example in which the opening and closing section 511 is opened.

For convenience of explanation, FIG. 5 B illustrates a structure in which the opening and closing part 511 protrudes to the outside of the main body MB, but the opening and closing part 511 is not limited thereto, and may be integrally formed with a portion of any one surface of the main body MB. A detailed description thereof will be omitted.

The composite sensor 510 may measure pressure applied to a closed space (e.g., internal space of the main body housing 530 of FIG. 5B) when the opening and closing part 511 is in a closed state (FIG. 5B), i.e., in a state that prevents entry of air from the outside; and the composite sensor 510 may measure external atmospheric pressure of the main body MB when the opening and closing part 511 is in an open state (FIG. 5C), i.e., in a state that allows entry of air from the outside.

The composite sensor driver 520 may include a voice coil, a magnet, a hall sensor, etc., and by using the same, the composite sensor driver 520 may drive the composite sensor 510 in a closed state or in an open state.

Figure 6:
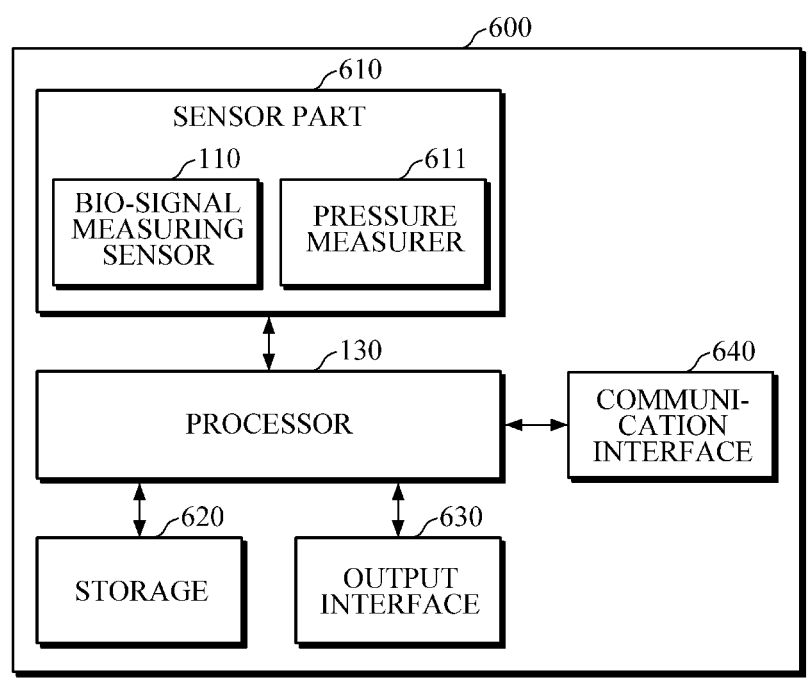
FIG. 6 is a block diagram illustrating an apparatus for estimating bio-information according to still another example embodiment of the present disclosure.

FIG. 6 is a block diagram illustrating an apparatus for estimating bio-information according to still another example embodiment of the present disclosure. Referring to FIG. 6, an apparatus 600 for estimating bio-information may include the processor 130, a sensor part 610, a storage 620, an output interface 630, and a communication interface 650. The sensor part 610 may include the bio-signal measuring sensor 110 and a pressure measurer 611. The bio-signal measuring sensor 110 and the processor 130 are described above with reference to FIG. 1, such that a description thereof will be omitted below.

The pressure measurer 611 may measure pressure applied to the inside of a closed space formed in the main body, and/or external atmospheric pressure. In this case, the pressure measurer 611 may refer to the internal pressure sensor 120 of FIG. 1, the internal pressure sensor 120 and the external atmospheric pressure sensor 410 of FIG. 4A, or the composite sensor 510 and the composite sensor driver 520 of FIG. 5A.

The storage 620 may store processing results of the bio-signal measuring sensor 110 and/or the processor 130. In addition, the storage 620 may store a variety of reference information required for estimating bio-information. For example, the reference information may include user characteristic information, such as a user's age, gender, health condition, and the like. In addition, the reference information may include information, such as reference contact pressure set for each user, a contact pressure estimation model, criteria for estimating bio-information, a bio-information estimation model, etc., but is not limited thereto.

In this case, the storage 620 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, etc., but is not limited thereto.

The output interface 630 may output the bio-signal measured by the bio-signal measuring sensor 110, the determined contact pressure between the bio-signal measuring sensor 110 and the object, guide information on the contact pressure, an estimated bio-information value generated by the processor 130, and the like.

For example, the output interface 630 may visually output data, processed by the bio-signal measuring sensor 110 or the processor 130, using a display module or may non-visually output the data by voice, vibrations, or tactile sensation using a speaker module, a haptic module, and the like.

In this case, a display area may be divided into two or more areas. For example, the output interface 630 may output the measured bio-signal value, the determined contact pressure, and the like in various forms of graphs in a first area. In this case, if contact pressure between the bio-signal measuring sensor 110 and the object fails to reach a predetermined reference range, the output interface 630 may output guide information for guiding a user to change the contact pressure. For example, along with an actual contact pressure between the bio-signal measuring sensor 110 and the object, the output interface 630 may visually display information on a predetermined range of contact pressure to be applied by the user during a measurement period of time on a display. Further, along with the information, the output interface 630 may output an estimated bio-information value in a second area. In this case, if the estimated bio-information value falls outside a normal range, the output interface 630 may output warning information in various manners, such as highlighting an abnormal value in red and the like, displaying the abnormal value along with the normal range, outputting a voice warning message, adjusting a vibration intensity, and the like.

The communication interface 640 may communicate with an external device by using wired or wireless communication techniques under the control of the processor 130, and may transmit and receive various data with the external device. For example, the communication interface 640 may transmit a bio-information estimation result to the external device, and may receive a variety of reference information required for estimating bio-information from the external device. In this case, the external device may include a cuff sphygmomanometer, and an information processing device, such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and the like. However, this is merely exemplary and is not intended to be limiting.

Figure 7:
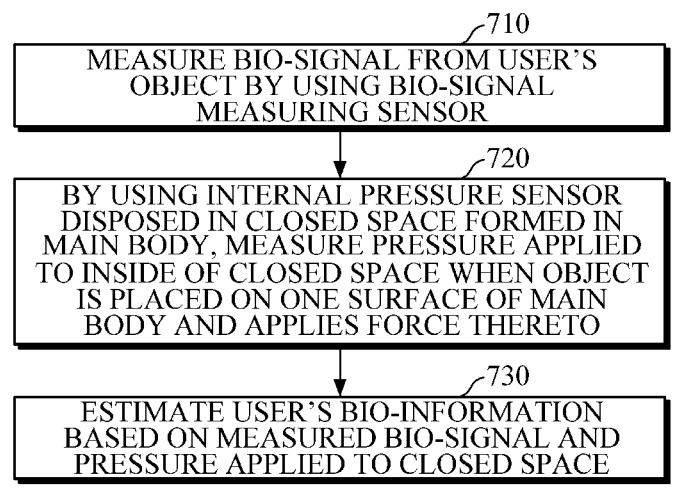
FIG. 7 is a flowchart illustrating a method of estimating bio-information according to an example embodiment of the present disclosure.

FIG. 7 is a flowchart illustrating a method of estimating bio-information according to an example embodiment of the present disclosure. The method of FIG. 7 is performed by the apparatuses 100, 400, 500, and 600 for estimating bio-information of FIGS. 1, 4A, 5A, and 6, which are described in detail above, and thus will be briefly described below in order to avoid redundancy.

First, the apparatus for estimating bio-information may measure a bio-signal from a user's object by using the bio-signal measuring sensor in operation 710. In this case, the bio-signal measuring sensor may be a PPG sensor and the bio-signal may be a PPG signal, but the present disclosure is not limited thereto.

Then, by using the internal pressure sensor disposed in a closed space formed in the main body, the apparatus for estimating bio-information may measure pressure applied to the inside of the closed space when the object is placed on one surface of the main body and applies force thereto in operation 720.

In this case, when the object is placed on one surface of the main body and applies force thereto, the apparatus for estimating bio-information may measure a change in volume of the closed space due to mechanical deformation of a structure (e.g., housing, block, etc.) having the closed space formed therein, and may measure the pressure applied to the inside of the closed space based on the measured change in volume of the closed space.

The closed space may be formed throughout the entire main body housing or may be formed in a portion of the internal space of the main body housing, or may be formed in a block disposed at a position where a relatively large mechanical deformation occurs. A detailed description thereof will be omitted.

Subsequently, the apparatus for estimating bio-information may estimate a user's bio-information based on the measured bio-signal and the pressure applied to the closed space in operation 730. The bio-information may be blood pressure but is not limited thereto.

In this case, the apparatus for estimating bio-information may determine contact pressure between the object and the bio-signal measuring sensor based on the measured pressure applied to the closed space, the measured external atmospheric pressure, a predetermined contact pressure estimation model, etc., and may estimate the user's bio-information based on the determined contact pressure. Upon determining the contact pressure between the object and the bio-signal measuring sensor, the apparatus for estimating bio-information may estimate the user's bio-information by analyzing a bio-signal according to the determined contact pressure between the object and the bio-signal measuring sensor.

For example, the apparatus for estimating bio-information may generate an oscillometric waveform envelope based on the measured PPG signal and the determined contact pressure, may extract one or more features from the generated oscillometric waveform envelope and/or preprocessed oscillometric waveform envelope, and may estimate the user's blood pressure based on the extracted features. A detailed description thereof will be omitted.

In this case, the apparatus for estimating bio-information may output at least one of the determined contact pressure between the object and the PPG sensor, guide information for guiding the user to change the contact pressure, and a bio-information estimation result, and may provide the user with the data. For example, the apparatus for estimating bio-information may visually output the data through a display module or may non-visually output the data by voice, vibrations, or tactile sensation using a speaker module, a haptic module, and the like.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
   a main body;
   a photoplethysmogram (PPG) sensor disposed in the main body and configured to measure a PPG signal from an object of a user;
   a composite sensor disposed in a closed space formed in the main body, and configured to measure, in a first time period, a change in volume of the closed space and determine a pressure applied to the closed space based on the change in the volume of the closed space when the object applies force to a surface of the main body, and measure, in a second time period different from the first time period, an external atmospheric pressure,
   wherein the composite sensor comprises
      an opening and closing part;
      a composite sensor driver configured to:
         set the opening and closing part to a closed state that prevents entry of external air when the composite sensor measures the pressure applied to the closed space in the first time period, and
         set the opening and closing part to an open state that allows entry of external air when the composite sensor measures the external atmospheric pressure in the second time period; and
      a processor configured to determine a contact pressure between the object and the PPG sensor based on the pressure applied to the closed space and the external atmospheric pressure, and estimate the bio-information of the user based on the PPG signal and the contact pressure.

2. The apparatus of claim 1, wherein the main body comprises a housing having the closed space formed therein.

3. The apparatus of claim 2, wherein the closed space is completely sealed.

4. The apparatus of claim 2, wherein the closed space is formed in only a portion of an internal space of the housing on a side of the apparatus.

5. The apparatus of claim 4, wherein the housing comprises an upper region in which a display is mounted, and a lower region that is opposite to the upper region,
   wherein the closed space is formed in the lower region of the housing.

6. The apparatus of claim 1, wherein the main body comprises a container having the closed space formed therein.

7. The apparatus of claim 6, wherein the container and the PPG sensor are disposed side-by-side on a same surface.

8. The apparatus of claim 1, further comprising a display configured to output at least one of the contact pressure between the object and the PPG sensor, guide information for guiding the user to change the contact pressure, and a bio-information estimation result.

9. A method of estimating bio-information by an electronic device, the method comprising:
   by using a photoplethysmogram (PPG) sensor, measuring a PPG signal from an object of a user;
   by using a composite sensor and disposed in a closed space formed in the electronic device, in a first time period, measuring a change in volume of the closed space and determining a pressure applied to an inside of the closed space based on the change in the volume of the closed space when the object contacts and applies force to a measurement surface of the PPG sensor of the electronic device;
   by using the composite sensor, in a second time period different from the first time period, measuring an external atmospheric pressure;
   by using a composite sensor driver included in the composite sensor, setting an opening and closing part of the composite sensor to a closed state that prevents entry of external air when the composite sensor measures the pressure applied to the closed space in the first time period;
   by using the composite sensor driver, set the opening and closing part to an open state that allows entry of external air when the composite sensor measures the external atmospheric pressure in the second time period;
   determining a contact pressure between the object and the PPG sensor based on the pressure applied to the closed space and the external atmospheric pressure; and
   estimating bio-information of the user based on the PPG signal and the contact pressure.

10. A non-transitory computer-readable storage medium storing a program that is executable by a computer to perform a method of estimating bio-information, the method comprising:
   obtaining a photoplethysmogram (PPG) signal that is measured from an object by an PPG sensor included in an electronic device;
   by using a composite sensor and disposed in a closed space formed in the electronic device, in a first time period, measuring a change in volume of the closed space and determining a pressure applied to an inside of the closed space based on the change in the volume of the closed space when the object contacts and applies force to a measurement surface of the PPG sensor of the electronic device;
   by using the composite sensor, in a second time period different from the first time period, measuring an external atmospheric pressure;
   by using a composite sensor driver included in the composite sensor, setting an opening and closing part of the composite sensor to a closed state that prevents entry of external air when the composite sensor measures the pressure applied to the closed space in the first time period;
   by using the composite sensor driver, set the opening and closing part to an open state that allows entry of external air when the composite sensor measures the external atmospheric pressure in the second time period;

determining a contact pressure between the object and the PPG sensor based on the pressure applied to the closed space and the external atmospheric pressure; and
estimating bio-information based on the PPG signal and the contact pressure.

* * * * *